US006947781B2

(12) United States Patent
Asada et al.

(10) Patent No.: US 6,947,781 B2
(45) Date of Patent: Sep. 20, 2005

(54) VIBRATORY VENOUS AND ARTERIAL OXIMETRY SENSOR

(75) Inventors: Haruhiko H. Asada, Lincoln, MA (US); Phillip Shaltis, Jackson, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 75 days.

(21) Appl. No.: 10/734,732

(22) Filed: Dec. 12, 2003

(65) Prior Publication Data

US 2004/0230107 A1 Nov. 18, 2004

Related U.S. Application Data

(60) Provisional application No. 60/433,570, filed on Dec. 13, 2002.

(51) Int. Cl.[7] .................................................. A61B 5/00
(52) U.S. Cl. ...................................... 600/335; 600/322
(58) Field of Search ................................ 600/322–323, 600/335, 309–310

(56) References Cited

U.S. PATENT DOCUMENTS

| | | | | |
|---|---|---|---|---|
| 3,835,839 | A | 9/1974 | Brown | 128/2.05 F |
| 3,878,502 | A | 4/1975 | Rochelle | 340/5 |
| 3,972,038 | A | 7/1976 | Fletcher et al. | 340/189 M |
| 3,972,320 | A | 8/1976 | Kalman | 128/2.1 A |

(Continued)

FOREIGN PATENT DOCUMENTS

| | | |
|---|---|---|
| DE | 31 50925 | 6/1983 |
| DE | 3609 913 | 10/1987 |
| EP | 0 467 853 | 7/1991 |
| EP | 0706 776 | 4/1996 |
| EP | 0 724 860 | 8/1996 |
| FR | 2 655 834 | 6/1991 |
| WO | WO 93/16636 | 9/1993 |
| WO | WO 98/17172 | 4/1998 |
| WO | WO 00/64338 | 11/2000 |
| WO | WO 01/67946 | 9/2001 |

OTHER PUBLICATIONS

Asada et al., The Ring Sensor: a New Ambulatory Wearable Sensor for Twenty–Four Hour Patient Monitoring, Proceeding of the 20th Annual International Conference of the IEEE Engineering in Medicine and Biology Society, Hong Kong, Oct. 29–Nov. 1, 1998.
Asada et al., Modeling of Finger Photoplethysmography for Wearable Sensors.
Asada et al., Artifact–Resistant Power–Efficient Design of Finger–Ring Plethysmographic Sensors, IEEE Transactions on Biomedical Engineering, vol. 48, No. 7, Jul. 2001.
Kamiya et al., Long–term ambulatory monitoring of indirect arterial blood pressure using a volume–oscillometric method, Med. & Biol. Eng. & Comput. 1985, 23, 459–465.
Yamakoshi et al., Current developments in non–invasive measurement of arterial blood pressure, J. Biomed.Eng., vol. 10, 129–137, 1988.
Beekvelt et al., Performance of near–infrared spectroscopy in measuring local $O_2$ consumption and blood flow in skeletal muscle, J. Appl. Physiol. vol. 90; pp. 511–519. 2001.
J.R. Womersley, Oscillatory Flow in Arteries: the Constrained Elastic Tube as a Model of Arterial Flow and Pulse Transmission, Phys. Med. Biol. 2, pp. 178–187, 1957.

Primary Examiner—Eric F. Winakur
Assistant Examiner—Matthew J Kremer
(74) Attorney, Agent, or Firm—Bromberg & Sunstein LLP (57) ABSTRACT

A method and an apparatus for distinguishing concentrations of blood constituents among distinct vascular components in situ. The method has steps of inducing periodic vibration, characterized by a frequency, in a limb of a person in such as manner as to selectively excite a resonant response in a specified blood vessel of the person, an artery or a vein, illuminating the limb of the person with a light source, and synchronously detecting a plethysmographic signal for discriminating response attributable to the specified blood vessel.

9 Claims, 6 Drawing Sheets

U.S. PATENT DOCUMENTS

| | | | |
|---|---|---|---|
| 4,063,410 A | 12/1977 | Welling | 58/38 R |
| 4,396,906 A | 8/1983 | Weaver | 340/347 D |
| 4,535,324 A | 8/1985 | Levental | 340/574 |
| 4,539,997 A | 9/1985 | Wesseling et al. | 128/167 |
| 4,799,062 A | 1/1989 | Sanderford, Jr. et al. | 342/450 |
| 4,825,872 A | 5/1989 | Tan et al. | 128/633 |
| 4,827,943 A | 5/1989 | Bornn et al. | 128/668 |
| 4,924,450 A | 5/1990 | Brashear et al. | 367/118 |
| 5,152,296 A | 10/1992 | Simons | 128/670 |
| 5,285,784 A | 2/1994 | Seeker | 128/633 |
| 5,297,548 A | 3/1994 | Pologe | 128/633 |
| 5,309,916 A | 5/1994 | Hatschek | 128/672 |
| 5,511,546 A | 4/1996 | Hon | 128/633 |
| 5,638,816 A * | 6/1997 | Kiani-Azarbayjany et al. | 600/316 |
| 5,638,818 A | 6/1997 | Diab et al. | 128/653.1 |
| 5,661,460 A | 8/1997 | Sallen et al. | 340/573 |
| 5,694,939 A | 12/1997 | Cowings | 128/671 |
| 5,735,800 A | 4/1998 | Yasukawa et al. | 600/503 |
| 5,738,102 A | 4/1998 | Lemelson | 128/671 |
| 5,771,001 A | 6/1998 | Cobb | 340/573 |
| 5,964,701 A | 10/1999 | Asada et al. | 600/300 |
| 6,263,222 B1 | 7/2001 | Diab et al. | 600/310 |
| 6,388,247 B2 | 5/2002 | Asada et al. | 250/221 |
| 2002/0169381 A1 | 11/2002 | Asada et al. | |
| 2002/0173709 A1 * | 11/2002 | Fine et al. | 600/335 |

* cited by examiner

VIBRATORY VENOUS AND ARTERIAL OXIMETRY SENSOR

The present application claims priority from U.S. Provisional Application, Ser. No. 60/433,570, filed Dec. 13, 2002, entitled "Vibratory Venous and Arterial Oximetry Sensor," which Application is incorporated herein by reference.

TECHNICAL FIELD

The present invention relates to a device and method for monitoring the blood constituents of a patient and, more particularly, for continuously measuring the arterial and venous oxygen saturations of a patient using an external perturbation.

BACKGROUND OF INVENTION

Traditional pulse oximetry has been recommended as a standard of care for nearly all areas of the medical care. By measuring the relative absorptions of different wavelengths of light, transilluminating a given region of the body (normally the fingertip or the earlobe), important systemic and physiological information related to the cardiovascular system can be measured. Currently, arterial blood flow is used as the main source of information because it provides a universal indication of the amount of oxygen available within circulating blood. Additionally, because of the pulsatile nature of the arteries, it is relatively easy to separate from other background absorption, as described in detail by Tremper et al., "Pulse Oximetry," *Anesthesiology*, vol. 70, (1989), pp. 98–108, incorporated herein by reference. However, under many circumstances, a cellular oxygen consumption provides a better measure of metabolic health, as discussed by Guyton et al., "Textbook of Medical Physiology," 9$^{th}$ ed., (W. B. Saunders Company, 1996), incorporated herein by reference.

It is well known that there is a critical balance of between the supply and demand for oxygen delivery within the body. In fact, global tissue hypoxia (severe oxygen deficiency) has been found to be an important indicator of serious illnesses, leading up to multi-organ failure and death. The level of tissue hypoxia provides information directly related to the "golden hours" of health care. These are the hours when recognition and treatment of the condition will provide maximal outcome benefit towards the patient's recovery. Until recently, however, there has not been a reliable measurement, or group of measurements for this indicator.

Clinical results suggest that a goal-directed therapy that utilizes early measurements of central venous oxygen saturation during resuscitation " . . . has significant short-term and long-term benefits . . . " (Rivers et al., "Early Goal-Directed Therapy in the Treatment of Severe Sepsis and Septic Shock," *The New England Journal of Medicine*, 345 (2001), pp. 1368–77). These benefits are believed to be the result of an earlier identification of the patients who are at a high risk for eventual cardiovascular collapse. By following a goal-directed therapy that includes the use of central venous oxygen saturation, researchers found that patient mortality rates related to shock could be reduced from 46% down to just over 30%.

Other studies have revealed that venous measurements can provide useful information about the function of the left heart as well as changes in cardiac output. Additionally, early localized, peripheral venous monitoring may be an extremely useful early indicator of internal systemic problems. For example, in low blood flow conditions, significant decreases in peripheral venous oxygen saturation will occur due to the fact that the slower blood flow provides local tissue with more time to extract available oxygen. The increased amount of extraction will be directly reflected by the decreases in the peripheral venous saturation.

Figure 1:
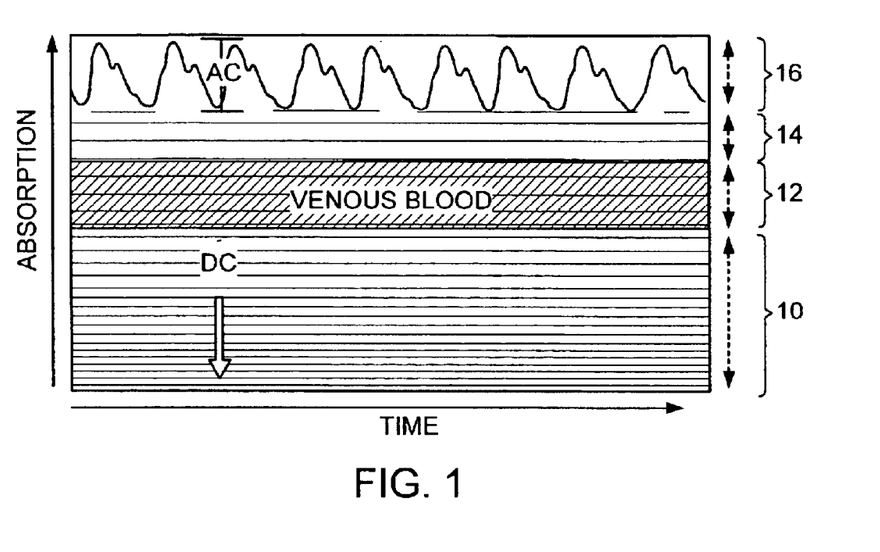
FIG. 1 depicts the time variation of absorption at two wavelengths for calculation of arterial oxygen saturation in accordance with prior art methods.

One method for measuring oxygen consumption consists of measuring the difference between arterial and venous oxygen saturations. Arterial measurements can easily be acquired because of their natural volumetric pulsations. These volumetric pulsations make it possible to optically differentiate arteries from the non-pulsatile background, as depicted in FIG. 1. Moreover, arterial volumetric pulsations are the key to modern pulse oximetry methods. Consequently, the arterial side of oxygen consumption measurements is fairly simple.

FIG. 1 depicts the optical absorption of body tissue. Optical absorption is plotted along the vertical axis, while the horizontal axis depicts time. The lower segment 10 represents absorption due to bone, skin, and other non-blood-bearing tissue. Segment 12 depicts absorption due to venous and capillary blood, while segment 14 represents the component of arterial blood flow that is non-pulsatile. Segments 10, 12, and 14, together, comprise a stationary and substantially novarying ('DC') component of the optical absorption of tissue. Segment 16 of the absorption is due to the pulsation of arterial blood volume. Traditional pulse oximeters measure the oxygen saturation at the artery by using an empirical formula relating arterial oxygen saturation (SaO2) to pulsatile photo-plethysmographic (PPG) signals at two wavelengths. In the prior art method, one or more light sources, such as LEDs, provide illumination, typically monochromatic, at one or more wavelengths. Photons from the LEDs pass through the skin. Although the photons illuminate in all directions, the average light path travels through a portion of the tissue and then back to a photodetector. Light detected at the photodetector has periodic (AC) and constant (DC) components, with the constant component primarily governed by light source intensity, ambient light, detector sensitivity, soft tissue, bone, venous blood, capillary blood, and non-pulsatile arterial blood. The AC component, on the other hand, captures the pulsating arterial blood.

Arterial blood flow is measured using LEDs emitting at the wavelengths specified with respect to the isobestic point of hemoglobin and oxygenated hemoglobin, at approximately 800 nanometers. At the isobestic wavelength $\lambda_i$, the optical absorption is insensitive to the fraction of oxygenated hemoglobin. 'RED' refers to a measurement performed at a wavelength shortward of $\lambda_i$, while 'IR' refers to a measurement performed at an infrared wavelength longward of $\lambda_i$.

The light transmitted through a tissue path including an arterial volume is monitored at each of the two (RED and IR) wavelengths, and the ratio, $$R = \frac{\ln\left(\frac{I_{out}(\text{systole})}{I_{out}(\text{diastole})}\right)_{RED}}{\ln\left(\frac{I_{out}(\text{systole})}{I_{out}(\text{diastole})}\right)_{IR}}$$

is taken as a measure of arterial oxygen saturation.

The pulsatile nature of the arterial signal differentiates signals attributed to the arterial blood from the one due to the venous blood and other surrounding tissue. The vein, however, does not pulsate, hence the standard oxygen saturation algorithm does not apply to the venous $O_2$ measurement. The difficulty of noninvasively measuring local venous saturation means that clinically acceptable oxygen consumption measurements are presently made through the use of blood drawn from highly invasive catheters. Unfortunately, since this type of measurement is both invasive and discrete (i.e., discontinuous) it is ordered mainly for critical care patients.

Current technologies for determination of venous saturation are extremely invasive and only provide information on the mixed venous saturation (a more global value) which is less sensitive to a low flow condition than a local venous saturation measurement. It is also desirable to provide a noninvasive technology that allows sensors to be used readily all over a hospital (emergency room, outpatient, etc.).

SUMMARY OF INVENTION

In accordance with preferred embodiments of the present invention, a method and an apparatus are provided for distinguishing concentrations of blood constituents among distinct vascular components in situ. The method has steps of:

a. inducing periodic vibration, characterized by a frequency, in a limb of a person in such as manner as to selectively excite a resonant response in a a specified blood vessel of the person;
  b. illuminating the limb of the person with a light source;
  c. detecting light from the light source that has traversed the specified blood vessel and generating a plethysmographic signal corresponding thereto; and
  d. synchronously detecting the plethysmographic signal for discriminating response attributable to the specified blood vessel.

In accordance with alternate embodiments of the invention, the specified blood vessel may be a vein, and the method may further include separately monitoring the plethysmographic signal attributable to the specified blood vessel and a plethysmographic signal attributable to second specified blood vessel. The step of illuminating the limb may include illuminating with two wavelengths of light and ratioing light detected at each of the two wavelengths of light in order to derive oxygen saturation of blood in the vein.

In accordance with yet further embodiments of the invention, the step of inducing vibration in the limb may include modulating air pressure applied to at least one inflatable pad enveloping the limb at least in part.

The method and apparatus described herein may advantageously be employed to measure both arterial and venous oxygen saturation, noninvasively, continuously, and concurrently. As will be described in the following sections, such a noninvasive, miniaturized design has wide applicability in the fields of both clinical health monitoring and personal fitness. In particular, this type of device is proficient at monitoring local muscular oxygen consumption rates as well as sudden changes in peripheral blood flow, as is known to occur in cases of sepsis and systemic shock.

BRIEF DESCRIPTION OF THE DRAWINGS

The invention will more readily be understood by reference to the following description taken with the accompanying drawings in which.

DETAILED DESCRIPTION OF PREFERRED EMBODIMENTS

Advances in noninvasive cardiovascular monitoring have greatly enhanced our understanding of systemic metabolism and oxygen delivery kinetics. For example, near-infrared spectroscopy (NIRS) has been shown to be an extremely sensitive modality for studying local differences in muscle $O_2$ consumption and delivery, as discussed in detail in Van Beekvelt et al, "Performance of near-infrared spectroscopy in measuring local $O_2$ consumption and blood flow in skeletal muscle," *Journal of Applied Physiology*, vol. 90, (2001), pp. 511–19, which is incorporated herein by reference. In addition to their high sensitivity, optically based monitoring designs are readily worn on the person and are capable of providing real-time information about the condition of the patient. These features afford such wearable, optical designs with a uniquely flexible applicability to the fields of both clinical health monitoring and enhanced fitness training.

Two primary considerations associated with venous measurements are: (1) how to differentiate a vein from both pulsatile and other non-pulsatile absorbers, (2) how to calculate oxygen saturation from a naturally non-pulsatile object such as a vein. Since, unlike the arteries, the veins do not pulsate, they temporally appear the same as most other absorbers within the body to photodetectors. In fact, given that simple photodetectors only measure light intensities and do not discriminate spatial intensity contributions, absorption due to veins is not normally differentiable from absorption due to surrounding tissue. Furthermore, as discussed, the key to traditional oxygen saturation measurements is the pulsatile nature of the arteries. Temporal volumetric pulsations make it possible to eliminate both path length and concentration dependencies from absorption equations. Unless these parameters are known a priori it is extremely difficult to optically calculate the saturation. Thus, it is necessary to employ a measurement strategy, which either eliminates the aforementioned issues or provides an alternate means for the measurement.

Figure 2A:
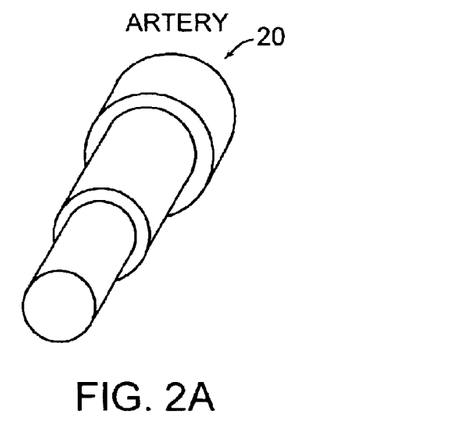
FIGS. 2A and 2B show the distinct mechanical features of an artery and a vein giving rise to distinct resonant behavior.
Figure 2B:
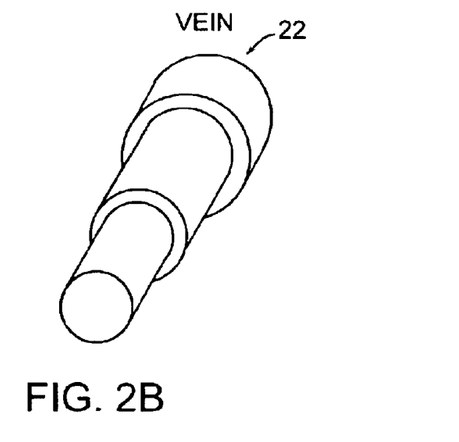

Anatomically, arteries and veins can have significantly different mechanical properties, as represented in FIGS. 2A and 2B, as exemplified by the difference between the elastic modulus (~1.1×10⁶ N m⁻²), of the femoral artery 20 shown in FIG. 2A, and that (~0.5×10⁶ N m⁻²) of the femoral vein 22 shown in FIG. 2B. The average elastic modulus of the femoral vein is thus approximately half that of the corresponding femoral artery.

Figure 3:
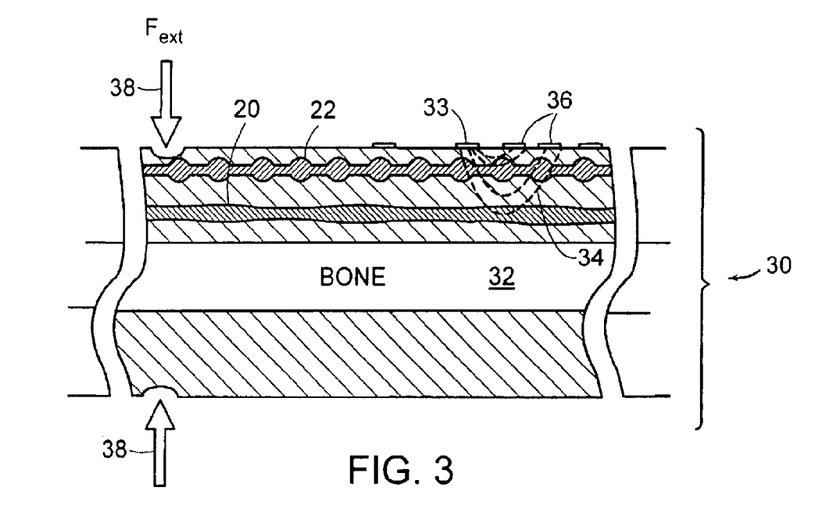
FIG. 3 depicts the principle of vibrational excitation of venous blood in accordance with preferred embodiments of the present invention, in order to provide a photoplethysmographically detectable venous signal.

Because of the distinct mechanical properties of the blood vessels, arteries and veins exhibit different dynamic responses to the same input. By surrounding the target vessels with an external perturbation cuff capable of inducing vascular volumetric pulsations, and by perturbing the system at the different resonant frequencies of the two vessels, it is possible to optically differentiate and localize their relative positions, as depicted schematically in FIGS. 8A and 8B, and as now discussed. FIG. 3 shows body tissue, such as a finger 30, including bone tissue 32, as well as an artery 20 and a vein 22. A light source 33, such as an LED, illuminates the tissue and its light, shown in this case, by way of example, as scattered light 34, is detected by one or more photodetectors 36. Application of an external force perturbation is indicated by arrows 38.

There are many advantages to adding a controlled perturbation. By optimizing the location, duration, and magnitude of the input, the stability of both the arterial and venous measurements may be optimized. Also since this method introduces a known venous volumetric pulsation, oxygen saturation may advantageously be measured using methods similar to traditional pulse oximeters. A final advantage of the monitoring method in accordance with the present invention is that, if other tissue types within the body are sufficiently decoupled, this method may advantageously be applied to other important measurements such as percentage of body fat.

Figure 4:
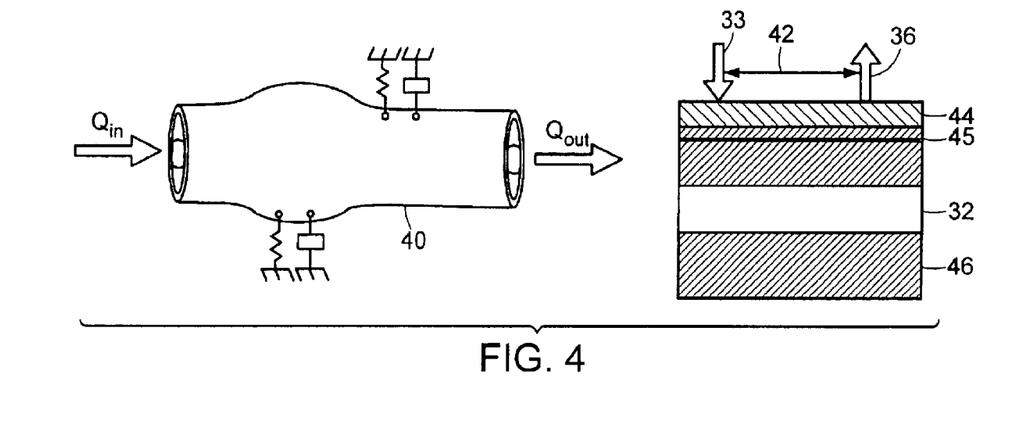
FIG. 4 depicts the characterization of a blood vessel in terms its mechanical resonant properties.

In order to optimize the sensor arrangement and input perturbation it is essential to develop an accurate opto-mechanical model of the sensor and arm, the elements of which are depicted in FIG. 4. To this end, a model for both the optical absorption and for the vascular kinematics has been developed. Both models are based on first principles and use fairly standard system assumptions. The mechanical model consists of a fluid-filled flexible tube 40 (substantially cylindrical) with constrained motion. Boundary conditions and input (magnitude and location) are empirical. The optical model utilizes a diffusive photon flux model to describe the light-skin interaction. Light source 33 and photodetector 36 are separated by a distance 42, while depths from the surface of skin 44 characterize blood vessel 45, bone 32, and muscle and adipose tissue 46. The mechanical and optical models are coupled, as now discussed.

Vascular Model: Fluid Mechanics

Womersley ("Oscillatory Flow in Arteries: the Constrained Elastic Tube as a Model of Arterial Flow and Pulse Transmission," *Physics in Medicine and Biology*, vol. 2: (1958), pp. 178–87) developed the basic fluid mechanics model for arterial blood flow in a flexible, constrained tube. The systems of equations express the balance of forces and the conservation of mass within the fluid and the tube and the continuity of stress and velocity components at the various boundaries.

The basic assumptions, which are standard for most cardiovascular system models, include: incompressible and Newtonian fluid that is laminar and axisymmetric. Under these conditions the linearized Navier-Stokes equation can be shown to be:

$$\frac{\partial v_r}{\partial t} = -\frac{1}{\rho}\frac{\partial p}{\partial r} + \nu\left\{\frac{\partial^2 v_r}{\partial r^2} + \frac{1}{r}\frac{\partial v_r}{\partial r} - \frac{v_r}{r^2} + \frac{\partial^2 v_r}{\partial x^2}\right\} \quad (1)$$

and $$\frac{\partial v_x}{\partial t} = -\frac{1}{\rho}\frac{\partial p}{\partial x} + \nu\left\{\frac{\partial^2 v_x}{\partial r^2} + \frac{1}{r}\frac{\partial v_x}{\partial r} + \frac{\partial^2 v_x}{\partial x^2}\right\} \quad (2)$$

with the equation of continuity written as, $$\frac{\partial v_x}{\partial t} + \frac{\partial v_r}{\partial r} + \frac{v_r}{r} = 0 \quad (3)$$

The variables are described as follows,
ρ=fluid density
ν=fluid kinematic viscosity
p=pressure
$v_r$, $v_x$=radial and axial velocities
r=radial component
x=axial component
t=time.

Vascular Model: Tube

The model for the motion of an elastic, cylindrical pipe with constraints is usually derived using membrane theory. The general assumptions associated with this particular model are that the tube is linear, viscoelastic, isotropic, homogenous, long, straight, and thin-walled. For these assumptions, the vascular dynamics are written as, $$\rho_w h \frac{\partial^2 u_r}{\partial t^2} = \left\{p - 2\mu\frac{\partial v_r}{\partial r}\right\}_{r=a} - \frac{Eh}{1-\sigma^2}\left\{\frac{u_r}{a^2} + \frac{\sigma}{a}\frac{\partial u_x}{\partial x}\right\} \quad (4)$$

and, $$\rho_w h \frac{\partial^2 u_x}{\partial t^2} = -\mu\left\{\frac{\partial v_r}{\partial r} + \frac{\partial v_x}{\partial x}\right\}_{r=a} + \frac{Eh}{1-\sigma^2}\left(\frac{\partial^2 u_x}{\partial x^2} + \frac{\sigma}{a}\frac{\partial u_r}{\partial x}\right) \quad (5)$$

where the boundary conditions are, $$v_r = \left.\frac{\partial u_r}{\partial t}\right|_{r=a} \quad (6a)$$

$$v_x = \left.\frac{\partial u_x}{\partial t}\right|_{r=a} \quad (6b)$$

$$v_r = 0|_{r=0} \quad (6c)$$

$$\frac{\partial v_x}{\partial r} = 0|_{r=0} \quad (6d)$$

The variables for these equations are defined as,
$\rho_w$=wall density
E=Young's modulus
σ=Poisson's as ratio
h=wall thickness
a=internal radius
$u_r$,$u_x$=radial and axial displacements
μ=modulus of rigidity.

These equations are used to analyze dynamic motion of a fluid-filled vessel under a given external perturbation.

In addition to the development of a mathematical description of the vibratory sensor, it is important to have an experimental model of the method that is simple enough to be easily described by the model, yet rich enough to be applicable to human testing situations. To this end, a model of a human arm, designated generally by numeral 50, has been designed and constructed, and is depicted schematically in FIG. 5. A peristaltic pump 52 on the left provides realistic arterial pulsations.

Figure 5:
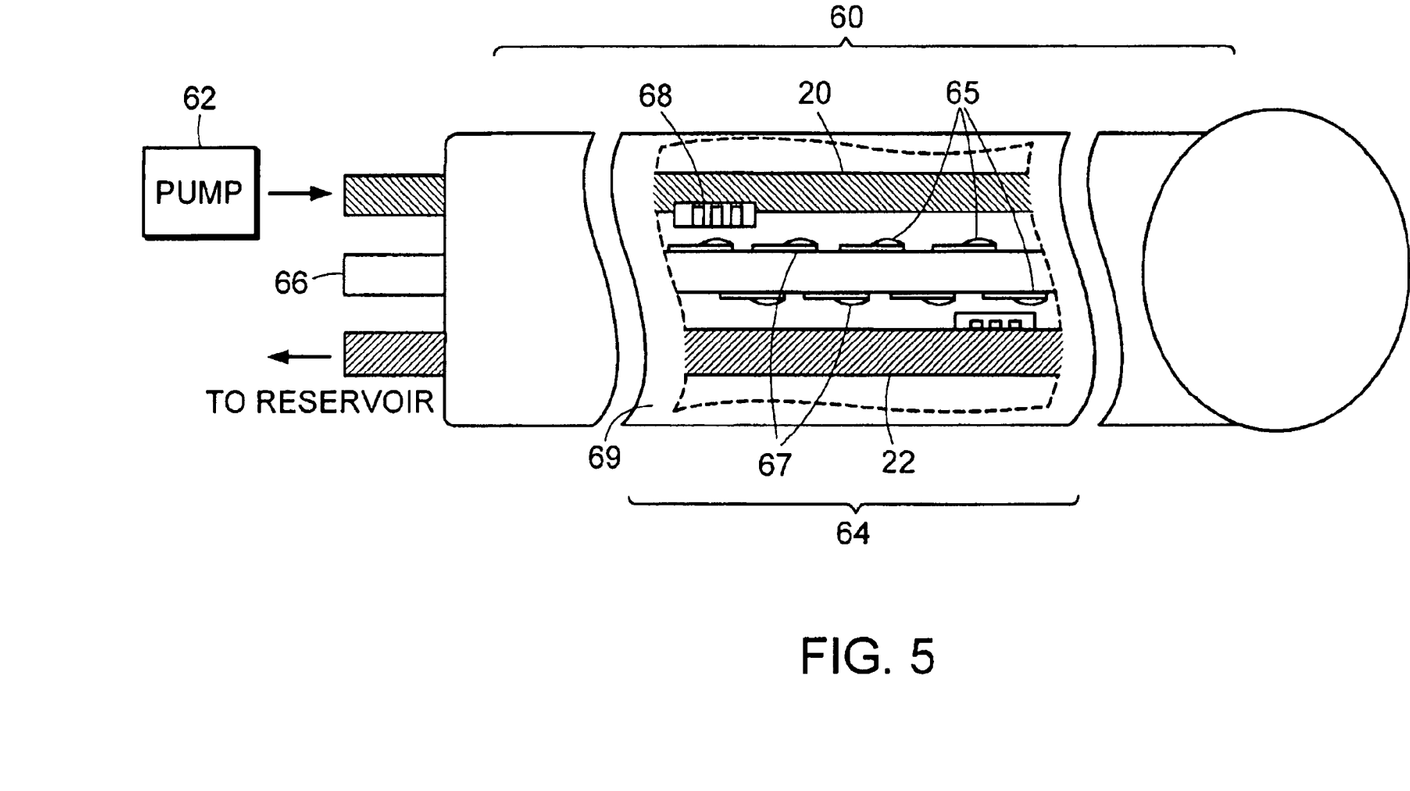
FIG. 5 is a schematic representation showing a network of vessels and sensors contained within a silicone gel-filled chamber of a model arm used to simulate operation of the present invention.

Phantom arm 60, shown in FIG. 5, is based on a standard arterial-venous venipuncture testing kit. The arm contains an extensive arterial and venous system, with pulsatile "blood" controlled by a 1 Hz peristaltic pump. Artery 20 and vein 22 are shown. Fluid-filled chamber 64 is an elastic membrane 69 filled with a silicone gel. Artery 20 is implemented by rubber tubing, while vein 22, implemented by balloon skin, runs parallel along the length of the arm. Between the two vessels is a steel rod 66 to which multiple photodetectors 65 and LEDs 67 are affixed. Identical sets of LED source and photodetectors face each of the respective vessels. Finally, two small, two-axis MEMS accelerometers 68 are suspended in the silicone on either side of the steel rod.

Elastic membrane 69, filled with silicone gel, provides a realistic approximation to human skin and a homogenous mixture of adipose and connective tissue, without muscles. These materials are quite reasonable to a first order because the main constraint against free vascular motion is the mixture of adipose tissue and connective tissue surrounding the vessels near the surface of the skin. The materials chosen for the two vessels also demonstrate reasonable approximations of the relative elastic modulii of the two vessels, and the respective model vessels.

The experimental setup of FIG. 5 demonstrates that different input perturbations produce unique arterial and venous responses that are optically differentiable in the presence of a dissipative media. All experiments were conducted using a pressure cuff, surrounding the phantom arm, set at a bias pressure of 40 mmHg. The cuff is then perturbed at a constant force using a simple, variable frequency oscillation. The frequency of the input was measured and recorded using an additional MEMS accelerometer attached to the oscillating part of the perturber. To minimize the influence of external lighting, the entire apparatus was placed inside a light-shielding container. The analog output of the photodetectors is sent through a current-to-voltage converting circuit and then through a $2^{nd}$ order, analog Butterworth low pass filter with cutoff frequency centered at 55 Hz. Finally, the analog signal is amplified and sent to a A/D converter.

Figure 6A:
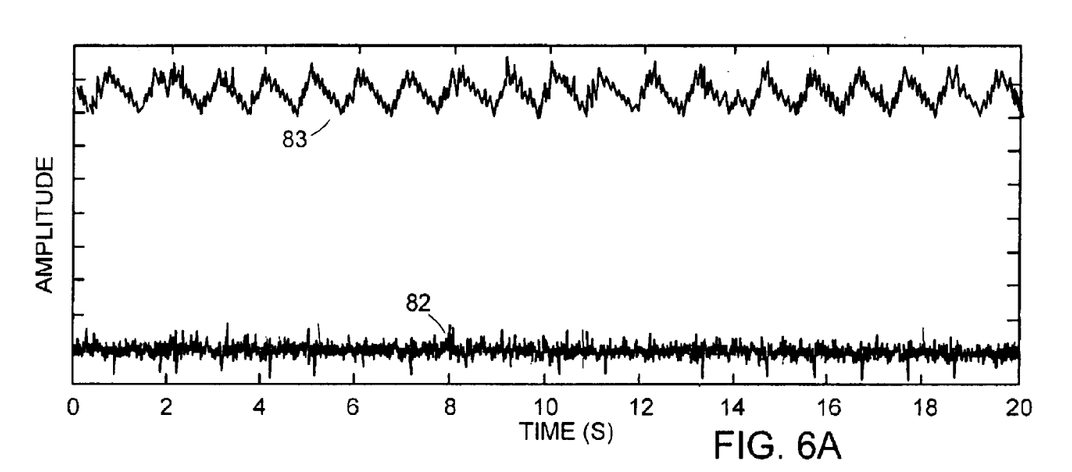
FIGS. 6A and 6B are representative time-scaled and frequency-scaled plots of the optical responses of an arterial and venous photodetector without input perturbation, showing only arterial pulsations.
Figure 6B:
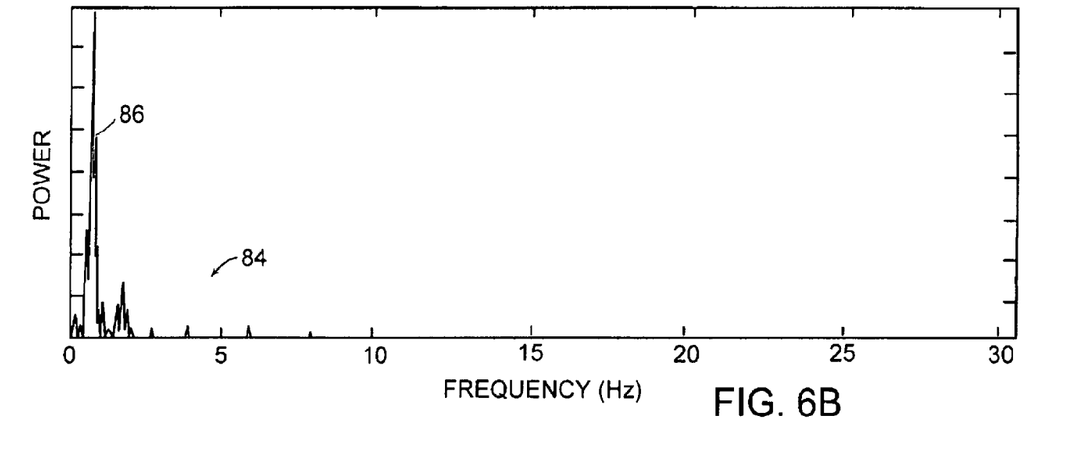
Figure 7A:
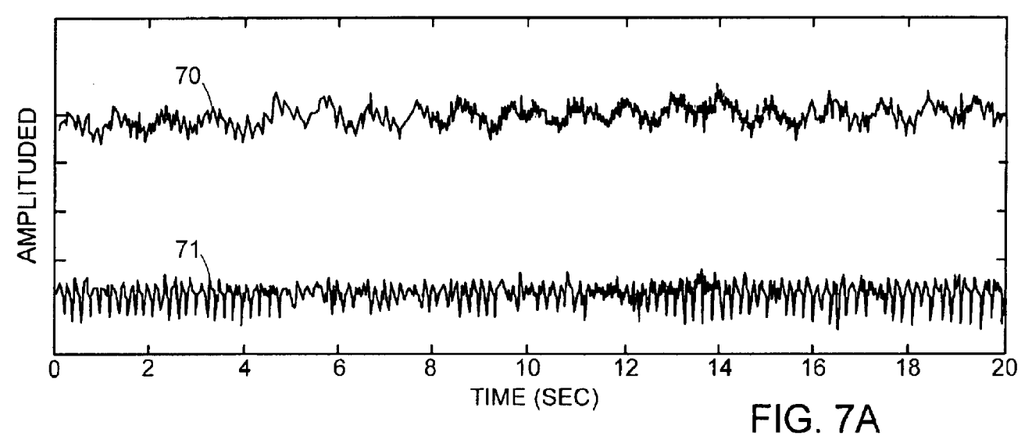
FIGS. 7A and 7B are representative time-scaled and frequency-scaled plots of the optical responses of an arterial and venous photodetector with a 5 Hz input perturbation in accordance with embodiments of the present invention.
Figure 7B:
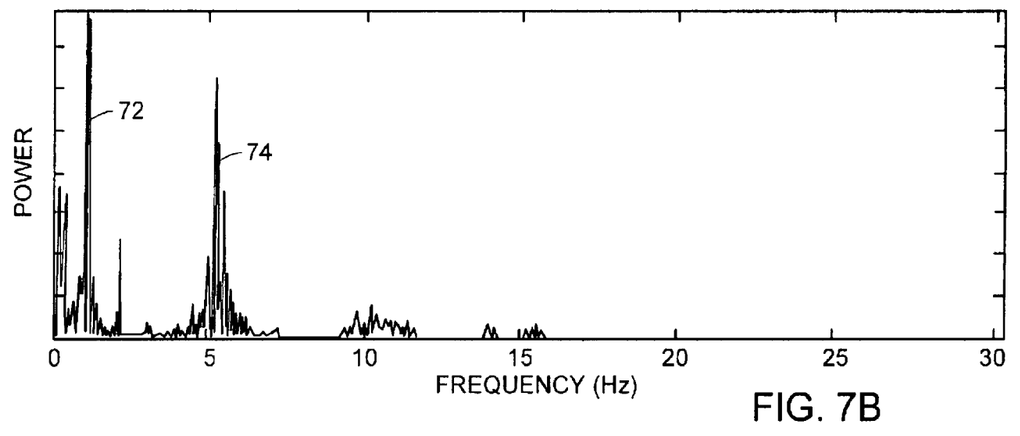

The previously described experimental setup was tested over a wide range of low frequency inputs at various loading magnitudes (1 Hz–50 Hz). All perturbation inputs were continuous sinusoidal pressure waves. The vein model was found to respond uniquely to preferred input frequencies as apparent in the time record of photodetector amplitude plotted in FIG. 7A where, for low frequency inputs (~5 Hz), significant venous pulsations 71 are optically detectable while significantly smaller pulsations at the same frequencies are identifiable in the arterial time record 71. The power spectrum of the detected signal is shown in FIG. 7B, with resonances dominated by the artery 72 and by the vein 74 are apparent. By way of comparison, In FIG. 6A, in the absence of external perturbation, no venous signal is apparent in either the time record 82 of FIG. 6A, or the power spectrum 84 of FIG. 6B. Trace 83 shows the pulsatile areterial time record, while trace 86 shows the power spectrum of the arterial signal.

These results indicate that even though the arteries and veins are coupled by surrounding adipose and connective tissue, the overall anatomical system may be perturbed such that only the vein is significantly excited. In addition to the vascular differentiability provided by the perturbation method, an optically detectable volumetric pulsation has also been created within the veins, making it possible to measure SvO2 using the basic pulse oximetry methodology.

Figure 8A:
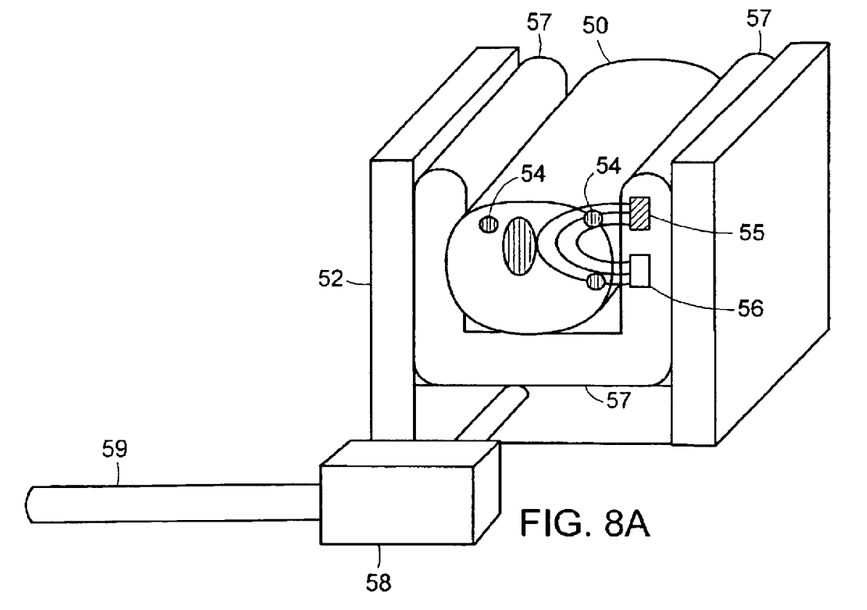
FIG. 8A is a schematic depiction of an apparatus for inducing vibrations in the limb of a person in accordance with embodiments of the present invention.

An apparatus for mechanically exciting the veins in a limb of a person is now described with reference to FIG. 8A where a schematic cross section is shown of an apparatus for vibratory excitation of venous blood flow in accordance with embodiments of the present invention. As shown in FIG. 8A, a limb 50, such as an arm or a leg, of a subject is encompassed by a fixture 52 on at least two opposing sides, with three sides shown in FIG. 8A. The cross sectional view of limb 50 shows multiple veins 54 which carry blood to be characterized by means of the present invention. A light source 55, which may include one or more light-emitting diodes (LEDs), illuminates the limb while light from source 55 is detected by one or more photodetectors 56. The LEDs may emit light in the visible or infrared, and may be particularly chosen to emit light at one or more specified wavelengths, such as wavelengths straddling the isobestic wavelength, as has been discussed above.

It is to be understood that a plurality of detectors may be employed and that the detectors may comprise an array. Furthermore, one or more of the plethysmographic sensors (i.e., source/detector combinations) may be disposed at a position on the body of the subject that is remote from the position where the blood vessels are being mechanically excited. This provides for additional information to be obtained based on phase delays of the signal with respect to the excitation which may be different for different blood vessel types due to differences in the wave propagation velocity among the blood vessel types.

Periodic pulsation of the venous tissue is induced by periodic inflation and deflation of one or more of pads 57 by modulating a source of pressurized fluid, such as air pressure supply 59 by a pressure valve and fluidic perturber 58. A pressure 'bias' may be provided by means of a pad 570 (shown in FIG. 8B) inflated to a constant pressure. Periodic changes in sensor output reflect changes in the volume of sampled blood due to vibratory excitation of the blood vessels.

Figure 8B:
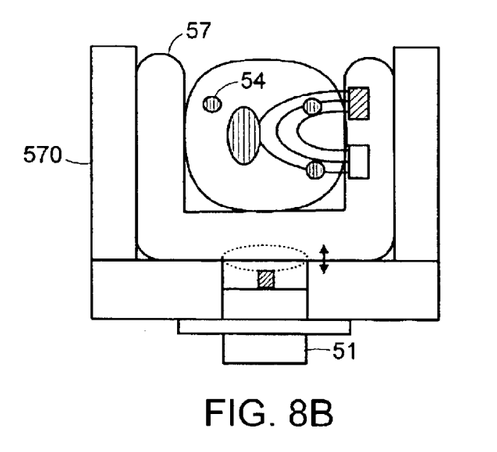
FIG. 8B is a schematic depiction of an apparatus for inducing vibrations in the limb of a person in accordance with other embodiments of the present invention.

An alternate embodiment of the invention is shown in the schematic cross section of FIG. 8B. Fluidic perturber 58 of FIG. 8A is replaced, in this embodiment, by a mechanical perturber 51 which acts with a periodic pushing and pulling of one or more of inflated pads 57 to achieve periodic pulsation of the venous tissue 54. Light transmitted through the periodically pressurized tissue is detected by photodetector 56 which generates a signal reflecting the volume of blood traversed.

In a preferred embodiment of the invention, the frequency of the perturbing excitation is swept, typically over the range of 0–30 Hz, thereby permitting distinct blood vessels to be identified on the basis of distinct properties of mechanical resonance.

The described embodiments of the invention are intended to be merely exemplary and numerous variations and modifications will be apparent to those skilled in the art. In particular, blood characteristics other than oxygen saturation may be measured employing the techniques described herein and is within the scope of the present invention. All such variations and modifications are intended to be within the scope of the present invention as defined in the appended claims.

We claim:

1. A method for distinguishing concentrations of blood constituents among distinct vascular components in situ, the method comprising:

a. inducing periodic vibration, characterized by a frequency, in a limb of a person in such a manner as to selectively excite a resonant response in a specified blood vessel of the person;

b. illuminating the limb of the person with a light source;

c. detecting light from the light source that has traversed the specified blood vessel and generating a plethysmographic signal corresponding thereto; and d. synchronously detecting the plethysmographic signal for a discriminating response attributable to the specified blood vessel.

2. A method in accordance with claim 1, wherein the specified blood vessel is a vein.

3. A method in accordance with claim 1, further including the step of separately monitoring the plethysmographic signal attributable to the specified blood vessel and a plethysmographic signal attributable to a second specified blood vessel.

4. A method in accordance with either of claim 1 or 3, wherein the step of illuminating the limb includes illuminating with two wavelengths of light.

5. A method in accordance with claim 4, further including the step of ratioing light detected at each of the two wavelengths of light in order to derive oxygen saturation of blood in the vein.

6. A method in accordance with claim 1, wherein the step of inducing vibration in the limb includes modulating air pressure applied to at least one inflatable pad enveloping the limb at least in part.

7. An apparatus for inducing a plethysmographic response due to blood in a specified blood vessel of a person, the apparatus comprising:

a. a vibrator for inducing periodic vibration, characterized by a frequency, in a limb of a person in such a manner a to selectively excite a resonant response in the specified blood vessel of the person;

b. a light source for illuminating the limb of the person;

c. a detector for detecting light from the light source that has traversed the specified blood vessel and for generating a plethysmographic signal corresponding thereto; and d. a signal processor for synchronously detecting the plethysmographic signal and for a discriminating response attributable to the specified blood vessel.

8. An apparatus in accordance with claim 7, wherein the vibrator is a mechanical perturber.

9. An apparatus in accordance with claim 7, wherein the vibrator is a fluidic perturber.

* * * * *

UNITED STATES PATENT AND TRADEMARK OFFICE
CERTIFICATE OF CORRECTION

PATENT NO. : 6,947,781 B2
DATED : September 20, 2005
INVENTOR(S) : Haruhiko H. Asada et al.

It is certified that error appears in the above-identified patent and that said Letters Patent is hereby corrected as shown below:

Column 1,
Line 4, add:
-- This invention was made with Government support under Grant No. DAMD17-02-2-2006, awarded by the Army. The Government has certain rights in the invention. --.

Column 10,
Line 10, replace "a to selectively excite a resonant response in the" with
-- as to selectively excite a resonant response in the --.

Signed and Sealed this

Tenth Day of January, 2006

JON W. DUDAS
*Director of the United States Patent and Trademark Office*